(12) United States Patent
Frey et al.

(10) Patent No.: US 9,080,134 B2
(45) Date of Patent: Jul. 14, 2015

(54) LINEAR ALKYLBENZENES FROM NATURAL OILS AND METHODS OF PRODUCING

(71) Applicant: UOP LLC, Des Plaines, IL (US)

(72) Inventors: Stanley J. Frey, Palatine, IL (US); Daniel L. Ellig, Arlington Heights, IL (US); Andrea G. Bozzano, Northbrook, IL (US); Geoffrey W. Fichtl, Chicago, IL (US); Debarshi Majumder, Forest Park, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/297,801

(22) Filed: Jun. 6, 2014

(65) Prior Publication Data

US 2015/0072916 A1 Mar. 12, 2015

Related U.S. Application Data

(60) Provisional application No. 61/833,354, filed on Jun. 10, 2013.

(51) Int. Cl.
| | |
|---|---|
| *C07C 2/64* | (2006.01) |
| *C07C 5/22* | (2006.01) |
| *C11D 3/34* | (2006.01) |

(Continued)

(52) U.S. Cl.
CPC .......... *C11D 3/3409* (2013.01); *C07C 1/22* (2013.01); *C07C 2/58* (2013.01); *C07C 2/70* (2013.01); *C07C 5/05* (2013.01); *C07C 5/2772* (2013.01); *C07C 5/333* (2013.01); *C07C 5/412* (2013.01); *C07C 7/00* (2013.01); *C07C 7/04* (2013.01); *C07C 7/20* (2013.01); *C07C 15/107* (2013.01); *C07C 303/04* (2013.01); *C07C 309/31* (2013.01); *C07C 2521/04* (2013.01); *C07C 2521/12* (2013.01); *C07C 2523/883* (2013.01); *C07C 2527/10* (2013.01); *C07C 2527/1206* (2013.01); *C07C 2529/00* (2013.01)

(58) Field of Classification Search
USPC .......................... 585/323, 314, 240, 446, 734
See application file for complete search history.

(56) References Cited

U.S. PATENT DOCUMENTS

| | | |
|---|---|---|
| 5,157,158 A | 10/1992 | Tejero et al. |
| 6,020,509 A | 2/2000 | Weerasooriya et al. |

(Continued)

FOREIGN PATENT DOCUMENTS

| | | |
|---|---|---|
| CN | 101709225 A | 5/2010 |
| CN | 101899318 A | 12/2010 |

(Continued)

OTHER PUBLICATIONS

Mohammad et al., "OVerview on the production of paraffin based-biofueld via catalytic hydrodeoxygenation", Renewable and Sustainable Energy Reviews, 2013, vol. 22, pp. 121-132.

(Continued)

*Primary Examiner* — Thuan D Dang (57) ABSTRACT

The production of linear alkylbenzene from a natural oil is provided. A method comprises the step of deoxygenating the natural oils to form a stream comprising paraffins. The paraffins are dehydrogenated to provide mono-olefins. Then, benzene is alkylated with the mono-olefins under alkylation conditions to provide an alkylation effluent comprising alkylbenzenes and benzene. Thereafter, the alkylbenzenes are isolated to provide the alkylbenzene product.

9 Claims, 3 Drawing Sheets

(51) Int. Cl.

| | | |
|---|---|---|
| *C07C 2/58* | (2006.01) | |
| *C07C 7/00* | (2006.01) | |
| *C07C 7/20* | (2006.01) | |
| *C07C 1/22* | (2006.01) | |
| *C07C 2/70* | (2006.01) | |
| *C07C 5/05* | (2006.01) | |
| *C07C 5/27* | (2006.01) | |
| *C07C 5/333* | (2006.01) | |
| *C07C 5/41* | (2006.01) | |
| *C07C 7/04* | (2006.01) | |
| *C07C 15/107* | (2006.01) | |
| *C07C 303/04* | (2006.01) | |
| *C07C 309/31* | (2006.01) | |

(56) References Cited

U.S. PATENT DOCUMENTS

| | | |
|---|---|---|
| 6,268,517 B1 | 7/2001 | Filler et al. |
| 6,641,623 B2 | 11/2003 | Matzat et al. |
| 7,311,815 B2 | 12/2007 | Abazajian |
| 7,432,310 B2 | 10/2008 | Steynberg et al. |
| 7,728,178 B2 | 6/2010 | Greager et al. |
| 7,781,630 B2 | 8/2010 | Glover et al. |
| 7,863,492 B2 | 1/2011 | Koper et al. |
| 7,880,049 B2 | 2/2011 | Dumesic et al. |
| 8,034,973 B2 | 10/2011 | Goncalvez De Almeida et al. |
| 8,053,615 B2 | 11/2011 | Cortright et al. |
| 8,067,657 B2 | 11/2011 | Santiago et al. |
| 8,075,642 B2 | 12/2011 | Dumesic et al. |
| 8,084,655 B2 | 12/2011 | Dindi et al. |
| 8,158,819 B2 | 4/2012 | Tejero et al. |
| 8,435,767 B2 | 5/2013 | Franklin et al. |
| 8,507,738 B2 | 8/2013 | Gomes et al. |
| 8,507,741 B2 | 8/2013 | Anumakonda et al. |
| 8,546,629 B2 | 10/2013 | Bozzano et al. |
| 8,580,540 B2 | 11/2013 | Dillon et al. |
| 8,592,638 B2 | 11/2013 | Aalto et al. |
| 8,748,679 B2 | 6/2014 | Fiato |
| 2008/0066374 A1 | 3/2008 | Herskowitz |
| 2008/0132435 A1 | 6/2008 | Ferreira Fontes et al. |
| 2009/0012323 A1 | 1/2009 | Van Rensburg et al. |
| 2011/0192077 A1 | 8/2011 | Miller |
| 2012/0132182 A1 | 5/2012 | Gunter et al. |
| 2013/0004646 A1 | 1/2013 | Franklin et al. |

FOREIGN PATENT DOCUMENTS

| | | |
|---|---|---|
| EP | 2006281 A2 | 12/2008 |
| EP | 2024467 A2 | 2/2009 |
| EP | 2495300 A1 | 9/2012 |
| EP | 2553072 | 2/2013 |
| GB | 704257 | 2/1954 |
| GB | 789032 | 1/1958 |
| GB | 848463 | 9/1960 |
| GB | 850355 | 10/1960 |
| WO | 0147841 A1 | 7/2001 |
| WO | 2010121591 A1 | 10/2010 |
| WO | 2012112828 A1 | 8/2012 |
| WO | 2012138423 A1 | 10/2012 |
| WO | 2013040367 A1 | 3/2013 |

OTHER PUBLICATIONS

Wang et al., "One-Step Hydrotreatment of Vegetable Oil to Produce High Quality Diesel-Range Alkanes", Oct. 2012, vol. 5, Issue 10, pp. 1974-1983.

Toba et al., "Hydrodeoxygenation of waste vegetable oil over sulfide catalysts", Catalysis Today, Apr. 2011, vol. 164, Issue 1, pp. 533-537.

Kubicka et al., "Deoxygenation of vegetable oils over sulfided Ni, Mo and NiMo catalysts", Applied Catalysis A: General, 2010, vol. 372, pp. 199-208.

LINEAR ALKYLBENZENES FROM NATURAL OILS AND METHODS OF PRODUCING

CROSS-REFERENCE TO RELATED APPLICATION

This application claims priority from Provisional Application No. 61/833,354 filed Jun. 10, 2013, the contents of which are hereby incorporated by reference in its entirety.

FIELD OF THE INVENTION

The present invention relates generally to alkylbenzenes from natural oils and methods for production of linear alkylbenzenes from natural oils. In an optional embodiment, biofuel may be co-produced with the renewable alkylbenzene.

BACKGROUND OF THE INVENTION

Linear alkylbenzenes are organic compounds with the formula $C_6H_5C_nH_{2n+1}$. While n can have any practical value, current commercial use of alkylbenzenes requires that n lie in the range of 10 to 16, or in the range of 8 to 15, or in the range of 10 to 13, or in the range of 12 to 15, or in the range of 9 to 14. These specific ranges are often required when the alkylbenzenes are used as intermediates in the production of surfactants for detergents. Because the surfactants created from alkylbenzenes are biodegradable, the production of alkylbenzenes has grown rapidly since their initial uses in detergent production in the 1960s. The linearity of the paraffin chain in the alkylbenzenes is key to the material's biodegradability and effectiveness as a detergent. A major factor in the final linearity of the alkylbenzenes is the linearity of the paraffin component While detergents made utilizing alkylbenzene-based surfactants are biodegradable, processes for creating alkylbenzenes are not based on renewable sources. Specifically, alkylbenzenes are currently produced from kerosene extracted from the earth. Due to the growing environmental concerns over fossil fuel extraction and economic concerns over exhausting fossil fuel deposits, there may be support for using an alternate source for biodegradable surfactants in detergents and in other industries.

Accordingly, it is desirable to provide linear alkylbenzenes with a high degree of linearity and with an increased content of "new carbon" and methods and systems for producing the linear alkylbenzenes from natural oils, i.e., oils that are not extracted from the earth. Further, it is desirable to provide renewable linear alkylbenzenes from easily processed triglycerides and fatty acids from vegetable, animal, nut, and/or seed oils. Optionally, biofuels may be co-produced with the linear alkylbenzenes. Other desirable features and characteristics of the present invention will become apparent from the subsequent detailed description of the invention and the appended claims, when taken in conjunction with the accompanying drawing and this background of the invention.

SUMMARY OF THE INVENTION

Methods for the co-production of an alkylbenzene product and biofuel from a natural oil are provided herein. In accordance with an exemplary embodiment, the method deoxygenates the natural oil to form a stream comprising paraffins. Then, a first portion of the paraffins are dehydrogenated to provide mono-olefins. In the method, the mono-olefins are used to alkylate benzene under alkylation conditions. As a result of alkylation, an alkylation effluent comprising alkylbenzenes and benzene is created. The alkylbenzenes are isolated from the effluent to provide the alkylbenzene product. A second portion of the paraffins is processed to form biofuel.

In another exemplary embodiment, a method is provided for the co-production of an alkylbenzene product and a biofuel from natural oil source triglycerides. In this embodiment, the triglycerides are deoxygenated to form a stream comprising water, carbon dioxide, carbon monoxide, propane, a first portion of paraffins, and a second portion of paraffins. This stream is fractionated to separate the first and second portions of paraffins. Then, the first portion of paraffins is dehydrogenated to provide mono-olefins. The mono-olefins are used to alkylate benzene under alkylation conditions to provide an alkylation effluent comprising alkylbenzenes and benzene. Thereafter, alkylbenzenes are isolated to provide the alkylbenzene product. The second portion of paraffins is processed to form biofuel.

In accordance with another embodiment, a method for co-production of an alkylbenzene product and biofuel from natural oil is provided. In the method, the natural oil is deoxygenated with hydrogen to form a stream comprising paraffins. A first portion of the paraffins is dehydrogenated to provide mono-olefins and hydrogen. According to the exemplary embodiment, the hydrogen provided by dehydrogenation is recycled to deoxygenate the natural oils. The mono-olefins are used to alkylate benzene under alkylation conditions to provide an alkylation effluent comprising alkylbenzenes and benzene. Then, the alkylbenzenes are isolated from the effluent to provide the alkylbenzene product. A second portion of the paraffins is processed to form biofuel.

BRIEF DESCRIPTION OF THE DRAWINGS

Embodiments of the present invention will hereinafter be described in conjunction with the following drawing figure wherein.

DETAILED DESCRIPTION

The following Detailed Description is merely exemplary in nature and is not intended to limit the invention or the application and uses of the invention. Furthermore, there is no intention to be bound by any theory presented in the preceding Background or the following Detailed Description.

As used in the present disclosure, the terms "renewably-based" or "renewable" denote that the carbon content of the renewable hydrocarbon (paraffins, olefins, aromatics, alkylbenzene, linear alkylbenzene or subsequent products prepared from renewable hydrocarbons), is from a "new carbon" source as measured by ASTM test method D6866-05, "Determining the Bio-based Content of Natural Range Materials Using Radiocarbon and Isotope Ratio Mass Spectrometry Analysis", hereby incorporated by reference in its entirety. This test method measures the $^{14}C/^{12}C$ isotope ratio in a sample and compares it to the $^{14}C/^{12}C$ isotope ratio in a standard 100 mass % bio-based material to give percent biobased content of the sample. Additionally, "Bio-based materials" are organic materials in which the carbon comes from recently, on a human time scale, fixated $CO_2$ present in the atmosphere using sunlight energy, photosynthesis. On land, this $CO_2$ is captured or fixated by plant life such as agricultural crops or forestry materials. In the oceans, the $CO_2$ is captured or fixated by photosynthesizing bacteria or phytoplankton. For example, a bio-based material has a $^{14}C/^{12}C$ isotope ratio greater than 0. Contrarily, a fossil-based material has a $^{14}C/^{12}C$ isotope ratio of about 0. The term "renewable" with regard to compounds such as hydrocarbons (paraffins, olefins, di-olefins, aromatics, alkylbenzene, linear alkylbenzene etc.) also refers to compounds prepared from biomass using thermochemical methods such as (e. g., Fischer-Tropsch catalysts), biocatalysts (e. g., fermentation), or other processes, for example.

A small amount of the carbon atoms in the atmospheric carbon dioxide is the radioactive isotope $^{14}C$. This $^{14}C$ carbon dioxide is created when atmospheric nitrogen is struck by a cosmic ray generated neutron, causing the nitrogen to lose a proton and form carbon of atomic mass 14 ($^{14}C$), which is then immediately oxidized, to carbon dioxide. A small but measurable fraction of atmospheric carbon is present in the form of $^{14}C$. Atmospheric carbon dioxide is processed by green plants to make organic molecules during the process known as photosynthesis. Virtually all forms of life on Earth depend on this green plant production of organic molecules to produce the chemical energy that facilitates growth and reproduction. Therefore, the $^{14}C$ that forms in the atmosphere eventually becomes part of all life forms and their biological products, enriching biomass and organisms which feed on biomass with $^{14}C$. In contrast, carbon from fossil fuels does not have the signature $^{14}C/^{12}C$ ratio of renewable organic molecules derived from atmospheric carbon dioxide. Furthermore, renewable organic molecules that biodegrade to $CO_2$ do not contribute to an increase in atmospheric greenhouse gases as there is no net increase of carbon emitted to the atmosphere.

Assessment of the renewably based carbon content of a material can be performed through standard test methods such as using radiocarbon and isotope ratio mass spectrometry analysis. ASTM International (formally known as the American Society for Testing and Materials) has established a standard method for assessing the bio-based content of materials. The ASTM method is designated ASTM-D6866.

The application of ASTM-D6866 to derive "biobased content" is built on the same concepts as radiocarbon dating, but without use of the age equations. The analysis is performed by deriving a ratio of the amount of radiocarbon ($^{14}C$) in an unknown sample compared to that of a modern reference standard. This ratio is reported as a percentage with the units "pMC" (percent modern carbon). If the material being analyzed is a mixture of present day radiocarbon and fossil carbon, which contains very low levels of radiocarbon, then the pMC value obtained correlates directly to the amount of biomass material present in the sample.

A renewable linear alkylbenzene product is provided which has the general chemical formula $C_6H_5C_nH_{2n+1}$ of which the carbon is predominantly modern carbon, as defined and measured by ASTM D6866, and not derived from petroleum, and has a linearity of the paraffin alkyl group preferably of greater than 80 mass % but more preferably greater than 90 mass % and most preferably of at least 92 mass %. Thus the alkylbenzene product contains at least 80 mass % of linear alkylbenzenes meaning alkylbenzenes wherein the paraffin alkyl group is a linear paraffin alkyl group. The renewable linear alkylbenzene consists of a benzene ring which comprises the portion of the chemical formula of $C_6H_5$ that is alkylated with linear paraffin which is described by the $C_nH_{2n+1}$ portion of the formula. Often, linear alkylbenzenes are sulfonated to produce a linear alkylbenzene sulfonate as a surfactant for use in detergents. For the purposes of use as material to produce a linear alkyl benzene sulfonate it is preferable that the paraffins carbon chain length (n in the chemical formula) of the alkyl group is in the range of 10 to 16, or in the range of 8 to 15, or in the range of 10 to 13, or in the range of 12 to 15, or in the range of 9 to 14. The carbons on the paraffin chain will be rich in carbon-14 isotope relative to that seen in petroleum derived paraffins. Carbon enriched in carbon-14 isotope is generally considered modern carbon, atmospheric carbon, or new carbon and is an indicator of how much renewable carbon is in the compound. Analytical methods such as ASTM D6866, as discussed above, can be used to determine the amount of carbon content that is modern carbon and not derived from petroleum by analyzing the amount of carbon-14 isotope in the compound. In one embodiment, the renewable linear alkylbenzene is at least 5 mass % modern carbon, in another embodiment more than 10 mass % modern carbon, in another embodiment more than 30 mass % modern carbon, and yet another embodiment more than 50 mass % modern carbon and still another embodiment greater than 60 mass % modern carbon.

The linearity of alkylbenzene product is mostly dependent on the linearity of the paraffins used to alkylate the benzene. It is a common rule of thumb by those skilled in the art that the linearity of a paraffin feed drops by about 5-7 mass % after dehydrogenation and alkylation. Therefore paraffin with 97 mass % linearity (or alternatively 3 mass % isoparaffin) would result in an alkylbenzene product with linearity around 90-92 mass %. This sets the requirement for paraffin linearity about 5-7 mass % higher than the specification for the alkylbenzene product. Typically the linearity of the paraffin product is measured by UOP 621, UOP 411, or UOP 732, which are standard test methods available from ASTM, which are hereby incorporated by reference in their entirety. Linear alkylbenzenes may be analyzed using ASTM Standard Test Method D4337 hereby incorporated by reference in its entirety.

Contrary to current theory, hydrocracking to a lower carbon chain length from a longer chain length is a very inefficient way to produce normal paraffins. For example, most plant oils have predominantly C16 and C18 carbon chains. If C10 to C13 carbon chains are required to make the desired alkylbenzene product, one might believe that cracking the hydrodeoxygenated C16 and C18 n-paraffins and the decarboxylated/decarbonylated C15 and C17 n-paraffins to the C10 to C13 range would be a suitable route. However, hydrocracking results in almost exclusively branched paraffins so very little of a hydrocracked product material would result in normal paraffins. Therefore to produce linear paraffins in the interesting carbon number ranges for linear alkyl benzene it is highly preferable to use oil with large amounts of C10, C12 and C14 carbon chain length fatty acids, these oils include coconut oil, palm kernel oil and babassu oil.

Alternatively, other natural oils may be used in the feedstock when the amount of nitrogen contained in components of the feedstock is low, such as less than 3 wt. ppm nitrogen, as shown in Examples 3 and 4, and or when the temperature for the deoxygenation is maintained below the temperature needed for hydrocracking or isomerization. Concentrations of nitrogen in nitrogen containing compounds as discussed herein refer to the amount of elemental nitrogen in a compound as measured by, for example, chemiluminescence techniques such as UOP Method 981 available from ASTM. PPM values are by weight unless stated otherwise. In addition, purification steps may be applied to feedstocks to adjust the nitrogen content to less than 3 wt. ppm nitrogen. Another technique to control the linearity of the paraffins produced is to control the temperature in the deoxygenation zone to a temperature less than that effective for isomerization or hydrocracking. In these embodiments, suitable natural oil feedstocks include those derived from plant or algae matter, and are often referred to as renewable oils. Natural oils are not based on kerosene or other fossil fuels. In certain embodiments, the natural oils include one or more of coconut oil, babassu oil, palm kernel oil, castor oil, cooking oil, and other vegetable, nut or seed oils. The natural oils typically comprise triglycerides, free fatty acids, or a combination of triglycerides and free fatty acids.

Figure 1:
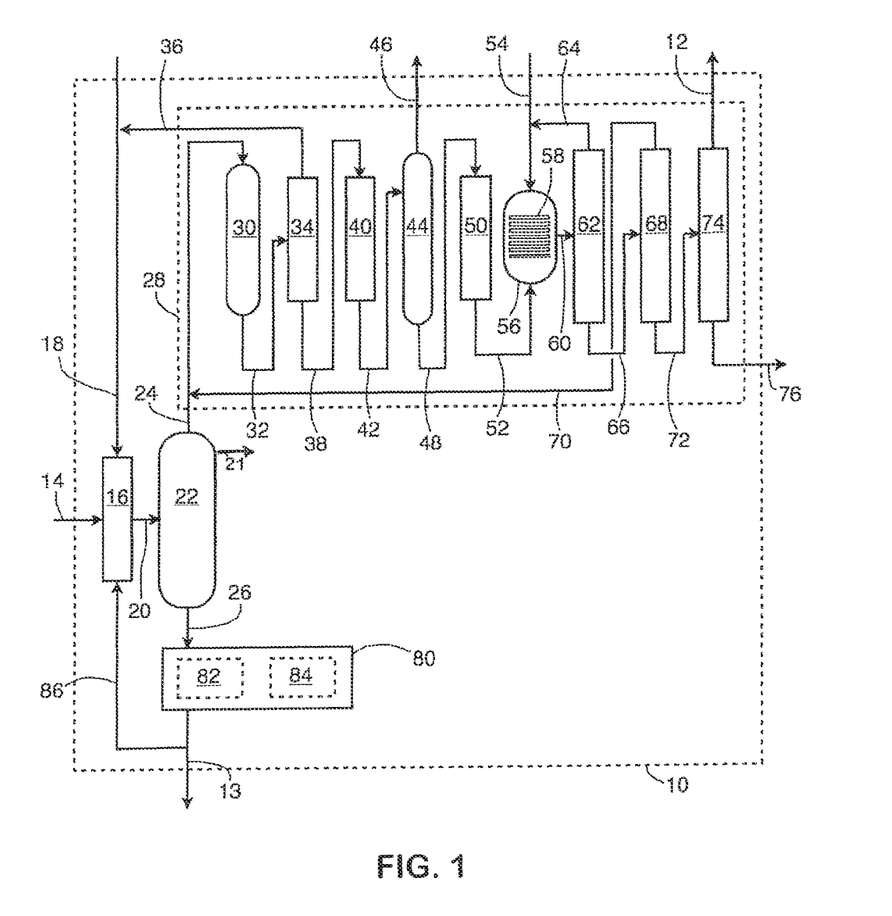
FIG. 1 schematically illustrates a system for co-production of alkylbenzene and biofuel in accordance with an exemplary embodiment.

Various embodiments contemplated herein relate to methods and systems for producing an alkylbenzene product from specific natural oils. In FIG. 1, an exemplary system 10 for producing an alkylbenzene product 12 from a specific natural oil feed 14 is illustrated. In one specific embodiment, a portion of the paraffins generated by the dehydrogenating step may be processed to co-produce a bio fuel, and FIG. 1 also shows this optional embodiment where a portion of the paraffins generated by the dehydrogenating step are used to produce biofuel 13. The natural oil feed is selected from the group consisting of coconut oil, palm kernel oil, babassu oil, and mixtures thereof. Natural oils are not based on kerosene or other fossil fuels. The natural oils comprise triglycerides, free fatty acids, or a combination of triglycerides and free fatty acids.

In the illustrated embodiment, the natural oil feed 14, which is selected from the group consisting of palm kernel oil, coconut oil, babassu oil and mixtures thereof, is delivered to a deoxygenation unit 16 which also receives a hydrogen feed 18. In the deoxygenation unit 16, the triglycerides and fatty acids in the feed 14 are deoxygenated and converted into normal paraffins. Structurally, triglycerides are formed by three, typically different, fatty acid molecules that are bonded together with a glycerol bridge. The glycerol molecule includes three hydroxyl groups (HO—) and each fatty acid molecule has a carboxyl group (COOH). In triglycerides, the hydroxyl groups of the glycerol join the carboxyl groups of the fatty acids to form ester bonds. Therefore, during deoxygenation, the fatty acids are freed from the triglyceride structure and are converted into normal paraffins. The glycerol is converted into propane, and the oxygen in the hydroxyl and carboxyl groups is converted into water, carbon dioxide, or carbon monoxide. The deoxygenation reaction for fatty acids and triglycerides are respectively illustrated as:

During the deoxygenation reaction, the length of a paraffin chain R″ created will vary by a value of one depending on the exact reaction pathway. It is understood that deoxygenation includes at least one of hydrodeoxygenation, decarboxylation, and decarbonylation, or any combination thereof. For instance, if carbon dioxide is formed, then the chain will have one fewer carbon than the fatty acid source. If water is formed, then the chain will match the length of in the fatty acid source. With these feed materials, many of the paraffins produced have even numbers of carbon atoms as shown in Example 1.

Operating conditions for the deoxygenating unit include pressures in the range of from about 250 to about 800 psig (about 1724 to about 5516 kPa) and temperatures in the range of from about 525° F. to about 700° F. (about 274° C. to about 371° C.) in one embodiment, from about 525° F. to about 640° F. (about 274° C. to about 338° C.) in another embodiment and from about 525° F. to about 590° F. (about 274° C. to about 310° C.) in another embodiment. Catalysts may include those containing one or more of Ni, Mo, Co, P, such as Ni—Mo, Ni—Mo—P, Ni—Co—Mo, or Co—Mo, on aluminas, silica, titania, zirconia, and mixtures thereof. Suitable hydrogen to hydrocarbon ratios include from about 1500 to 8000, from about 3500 to 7600, and from about 3500-6000 standard cubic feet per barrel of feedstock (scf/B). Suitable space velocities include 0.2-3.0 hr$^{-1}$ LHSV. Conditions are selected to minimize cracking or isomerizing the paraffins.

In FIG. 1, a deoxygenated stream 20 containing normal paraffins, water, carbon dioxide, carbon monoxide, and propane exits the deoxygenation unit 16 and is fed to a separator 22. The separator 22 may be a multi-stage fractionation unit, distillation system or similar known apparatus. In any event, the separator 22 removes the water, carbon dioxide, carbon monoxide, and propane (stream 21) from the deoxygenated stream 20. Further, the separator 22 may provide a first portion of paraffins 24 and a second portion of paraffins 26. In certain embodiments, the first portion of paraffins 24 has carbon chain lengths of $C_{10}$ to $C_{14}$. In other embodiments, the first portion of paraffins 24 has carbon chain lengths having a lower limit of $C_L$, where L is an integer from four (4) to thirty-one (31), and an upper limit of $C_U$, where U is an integer from five (5) to thirty-two (32). The optional second portion of paraffins 26 may have carbon chains shorter than, longer than, or a combination of shorter and longer than, the chains of the first portion of paraffins 24. In a specific embodiment, the first portion of paraffins 24 comprises paraffins with $C_{10}$ to $C_{13}$ chains and the optional second portion of paraffins 26 comprises paraffins with $C_{14}$ to $C_{18}$ chains.

As shown in FIG. 1, the first portion of paraffins 24 is introduced to an alkylbenzene production zone 28. Specifically, the first portion of paraffins 24 is fed into a dehydrogenation unit 30 in the alkylbenzene production unit 28. In the dehydrogenation unit 30, the first portion of paraffins 24 are dehydrogenated into mono-olefins of the same carbon numbers as the first portion of paraffins 24. Typically, dehydrogenation occurs through known catalytic processes, such as the commercially popular Pacol process. Di-olefins (i.e., dienes) and aromatics are also produced as an undesired result of the dehydrogenation reactions as expressed in the following equations:

Mono-olefin formation: $C_XH_{2X+2} \rightarrow C_XH_{2X}+H_2$

Di-olefin formation: $C_XH_{2X} \rightarrow C_XH_{2X-2}+H_2$

Aromatic formation: $C_XH_{2X-2} \rightarrow C_XH_{2X-6}+2H_2$

Operating conditions for the dehydrogenation unit include space velocities from about 5 to about 50 hr$^{-1}$ LHSV and from about 20 to about 32 hr$^{-1}$ LHSV; pressures from about 5 psig to about 50 psig and from about 15 psig; to about 25 psig; temperatures from about 400-500° C. and from about 440 to about 490° C., and hydrogen to hydrocarbon mole ratios from about 1-12 and from about 3-7. An example of a suitable catalyst is a Pt on alumina catalyst where platinum is attenuated with an attenuator metal. Another suitable catalyst is described in U.S. Pat. No. 6,177,381 hereby incorporated by reference. The unit may be operated dry or with water injection up to about 2000 mass-ppm water.

In FIG. 1, a dehydrogenated stream 32 exits the dehydrogenation unit 30 comprising mono-olefins and hydrogen, as well as some di-olefins and aromatics. The dehydrogenated stream 32 is delivered to a phase separator 34 for removing the hydrogen from the dehydrogenated stream 32. As shown, the hydrogen exits the phase separator 34 in a recycle stream of hydrogen 36 that can be added to the hydrogen feed 18 to support the deoxygenation process upstream.

At the phase separator 34, a liquid stream 38 is formed and comprises the mono-olefins and any di-olefins and aromatics formed during dehydrogenation. The liquid stream 38 exits the phase separator 34 and enters a selective hydrogenation unit 40, such as a DeFine reactor. The hydrogenation unit 40 selectively hydrogenates at least a portion of the di-olefins in the liquid stream 38 to form additional mono-olefins. As a result, an enhanced stream 42 is formed with an increased mono-olefin concentration.

As shown, the enhanced stream 42 passes from the hydrogenation unit 40 to a lights separator 44, such as a stripper column, which removes a light end stream 46 containing any lights, such as butane, propane, ethane and methane, that resulted from cracking or other reactions during upstream processing. With the light ends 46 removed, stream 48 is formed and may be delivered to an aromatic removal apparatus 50, such as a Pacol Enhancement Process (PEP) unit available from UOP. As indicated by its name, the aromatic removal apparatus 50 removes aromatics from the stream 48 and forms a stream of mono-olefins 52.

In FIG. 1, the stream of mono-olefins 52 and a stream of benzene 54 are fed into an alkylation unit 56. The alkylation unit 56 holds a catalyst 58, such as a solid acid catalyst, that supports alkylation of the benzene 54 with the mono-olefins 52. Fluorided silica-alumina, hydrogen fluoride (HF), aluminum chloride ($AlCl_3$), and zeolitic catalysts are examples of major catalysts in commercial use for the alkylation of benzene with linear mono-olefins and may be used in the alkylation unit 56. As a result of alkylation, alkylbenzene, typically called linear alkylbenzene (LAB), is formed according to the reaction:

and are present in an alkylation effluent 60.

Suitable operating conditions for the alkylation unit include space velocities from 1 to about 10 $hr^{-1}$ LHSV, pressures to maintain liquid phase operation such as about 300 to about 600 psig, temperatures in the range of from about 80° C. to about 180° C. and 120° C. to about 170° C., benzene to olefin mole ratios of about 3 to about 40 and about 8 to about 35.

Surplus amounts of benzene 54 are supplied to the alkylation unit 56 to achieve high degree of desired alkylation. Therefore, the alkylation effluent 60 exiting the alkylation unit 56 contains alkylbenzene and unreacted benzene. Further the alkylation effluent 60 may also include some unreacted paraffins. In FIG. 1, the alkylation effluent 60 is passed to a benzene separation unit 62, such as a fractionation column, for separating the unreacted benzene from the alkylation effluent 60. This unreacted benzene exits the benzene separation unit 62 in a benzene recycle stream 64 that is delivered back into the alkylation unit 56 to reduce the volume of fresh benzene needed in stream 54.

As shown, a benzene-stripped stream 66 exits the benzene separation unit 62 and enters a paraffinic separation unit 68, such as a fractionation column. In the paraffinic separation unit 68, unreacted paraffins are removed from the benzene-stripped stream 66 in a recycle paraffin stream 70, and are routed to and mixed with the first portion of paraffins 24 before dehydrogenation as described above.

Further, an alkylbenzene stream 72 is separated by the paraffinic separation unit 68 and is fed to an alkylate separation unit 74. The alkylate separation unit 74, which may be, for example, a multi-column fractionation system, separates a heavy alkylate bottoms stream 76 from the alkylbenzene stream 72.

As a result of the post-alkylation separation processes, the linear alkylbenzene product 12 is isolated and exits the apparatus 10. It is noted that such separation processes are not necessary in all embodiments in order to isolate the alkylbenzene product 12. For instance, the alkylbenzene product 12 may be desired to have a wide range of carbon chain lengths and not require any fractionation to eliminate carbon chains longer than desired, i.e., heavies or carbon chains shorter than desired, i.e., lights. Further, the feed 14 may be of sufficient quality that no fractionation is necessary despite the desired chain length range. In certain embodiments, the feed 14 is substantially homogeneous and comprises free fatty acids within a desired range. For instance, the feed may be entirely Lauric free fatty acid such that all the free fatty acids of the feed have 12 carbon atoms. Alternatively, the feed 14 may comprise triglycerides and free fatty acids that all have carbon chain lengths appropriate for a desired alkylbenzene product 12.

In certain embodiments, the natural oil source is castor, and the feed 14 comprises castor oils. Castor oils consist essentially of $C_{18}$ fatty acids with an additional, internal hydroxyl groups at the carbon-12 position. For instance, the structure of a castor oil triglyceride is:

During deoxygenation of a feed 14 comprising castor oil, it has been found that some portion of the carbon chains are cleaved at the carbon-12 position. Thus, deoxygenation creates a group of lighter paraffins having $C_{10}$ to $C_{11}$ chains resulting from cleavage during deoxygenation, and a group of non-cleaved heavier paraffins having $C_{17}$ to $C_{18}$ chains. The lighter paraffins may form the first portion of paraffins 24 and the heavier paraffins may form the second portion of paraffins 26. It should be noted that while castor oil is shown as an example of an oil with an additional internal hydroxyl group, others may exist. Also, it may be desirable to engineer genetically modified organisms to produce such oils by design. Another embodiment may involve a pathway such as found in U.S. application Ser. No. 13/712,181. As such, any oil with an internal hydroxyl group may be a desirable feed oil. Also, it may be desirable to modify regular vegetable oils, such as soybean or jatropha oil such that they contain internal hydroxyl groups, similar to the structure of castor oil, and thus the modified oil would behave similarly to castor oil upon deoxygenation, producing a first and second portion of paraffins. Examples of such modifications are described in U.S. application Ser. No. 13/712,181 hereby incorporated by reference in its entirety The second portion of paraffins 26 may be recovered or may be further processed. As shown in FIG. 1, the second portion of paraffins 26 may be optionally fed to a system 80 for producing biofuel 13 such as diesel or jet fuel. Typically, no further deoxygenation is needed in the biofuel production system 80. Rather, in the system 80, the second portion of paraffins 26 are typically isomerized in an isomerization unit 82 or cracked in a cracking unit 84 to create the isoparaffins of equal or lighter molecular weight than the second portion of paraffins 26. Hydrogen not consumed during these processes is separated out from the resulting biofuel 13 to form a hydrogen stream 86 that is recycled to the deoxygenation unit 16. While shown feeding the deoxygenation unit 16 directly, the hydrogen stream 86 could be fed to hydrogen feed 18.

In order to create green diesel, the biofuel production system 80 primarily isomerizes the second portion of paraffins 26 with minimal cracking. For the production of biojet or green jet fuel, some cracking is performed in order to obtain smaller molecules (with reduced molecular weight) to meet the more stringent freeze points required by jet specifications.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

The product produced herein is a linear alkylbenzene product comprising: alkylbenzenes having the formula $C_6H_5C_nH_{2n+1}$ wherein n is from 12 to 13; wherein the alkylbenzenes have at least 7 mass % modern carbon as measured by ASTM Method 6866; and wherein at least 80 mass % of the alkylbenzenes having the formula $C_6H_5C_nH_{2n+1}$ wherein n is from 12 to 13, have linear alkyl groups. In other words, linear alkyl groups are present in at least 80 mass % of the alkylbenzenes produced where the alkylbenzenes have the formula $C_6H_5C_nH_{2n+1}$ wherein n is from 12 to 13. In other embodiments at least 90 mass % of the alkylbenzenes have linear alkyl groups or at least 91 mass % of the alkylbenzenes have linear alkyl groups. In other embodiments the alkylbenzenes have at least 10 mass % modern carbon, 30 mass % modern carbon, 50 mass % modern carbon or 60 mass % modern carbon as measured by ASTM Method 6866. In other embodiments, n is from 12 to 15, or n is from 10-13 or n is from 10 to 16.

The linear alkylbenzene may be sulfonated to provide a linear alkylbenzene sulfonate product comprising: alkylbenzene sulfonate compounds having the formula $C_6H_5C_nH_{2n+1}C_6H_4SO_3H$ wherein n is from 12 to 13; wherein the alkylbenzene sulfonate compounds have at least 5 mass % modern carbon as measured by ASTM Method 6866; wherein the alkyl group is a linear alkyl group for at least 80 mass % of the alkylbenzene sulfonate compounds having the formula $C_nH_{2n+1}C_6H_4SO_3H$ wherein n is from 12 to 13. In other embodiments alkyl group is a linear alkyl group for at least 90 mass % of the linear alkylbenzene sulfonates have linear alkyl groups or at least 91 mass % of the linear alkylbenzene sulfonates. In other embodiments the linear alkylbenzene sulfonate has at least 10 mass % modern carbon, or 30 mass % modern carbon, or 50 mass % modern carbon, or 60 mass % modern carbon as measured by ASTM Method 6866. In other embodiments, n is from 12 to 15, or n is from 10-13, or n is from 10 to 16.

Example 1

Coconut oil was deoxygenated to produce paraffins which were then used in the production of renewable linear alkylbenzene. During this operation paraffins were produced with different degrees of linearity. The deoxygenation was performed over a Ni—Mo catalyst supported on alumina. As can be seen in Table 1 with fully active catalyst much isomerization is apparent. After the catalyst is attenuated it loses it isomerization activity and high linearity is obtained. Commensurate with that decarboxylation activity is lost and as shown by the ever increasing even to odd carbon number ratio with time which also increases with increasing carbon number. It is surprising that the odd numbered carbon chain lengths increase relative to the even with increasing carbon number. This indicates that higher carbon chain length oils would provide a smoother carbon chain distribution than lower carbon number chain lengths.

TABLE 1

| | Hours on stream | | | | |
|---|---|---|---|---|---|
| | 21 | 42 | 74 | 94 | 118 |
| Temperature (F.) | 594 | 615 | 612 | 612 | 621 |
| Pressure (psig) | 600 | 600 | 600 | 600 | 600 |
| LHSV (hr−1) | 0.72 | 1 | 1 | 1 | 1 |
| H2:HC (SCFB) | 5277 | 3800 | 3800 | 3800 | 3800 |
| Iso % by C# Ratio of isoparaffins between subject n-paraffin to next lightest n-paraffin | | | | | |
| Isos between nC8 and nC9/nC9 | 26.9% | 4.2% | 2.1% | 2.4% | 2.7% |
| Isos between nC9 and nC10/nC10 | 7.8% | 1.2% | 0.9% | 1.1% | 1.4% |
| Isos between nC10 and nC11/nC11 | 4.7% | 0.6% | 0.6% | 0.6% | 1.0% |
| Isos between nC11 and nC12/nC12 | 1.6% | 0.8% | 0.7% | 0.7% | 0.9% |
| Isos between nC12 and nC13/nC13 | 6.0% | 1.2% | 1.1% | 1.2% | 1.7% |
| Isos between nC13 and nC14/nC14 | 2.2% | 1.0% | 0.7% | 0.8% | 1.0% |
| Isos > nC14/nC14+ | 4.1% | 0.4% | 0.4% | 0.5% | 0.6% |

Example 2

Figure 2:
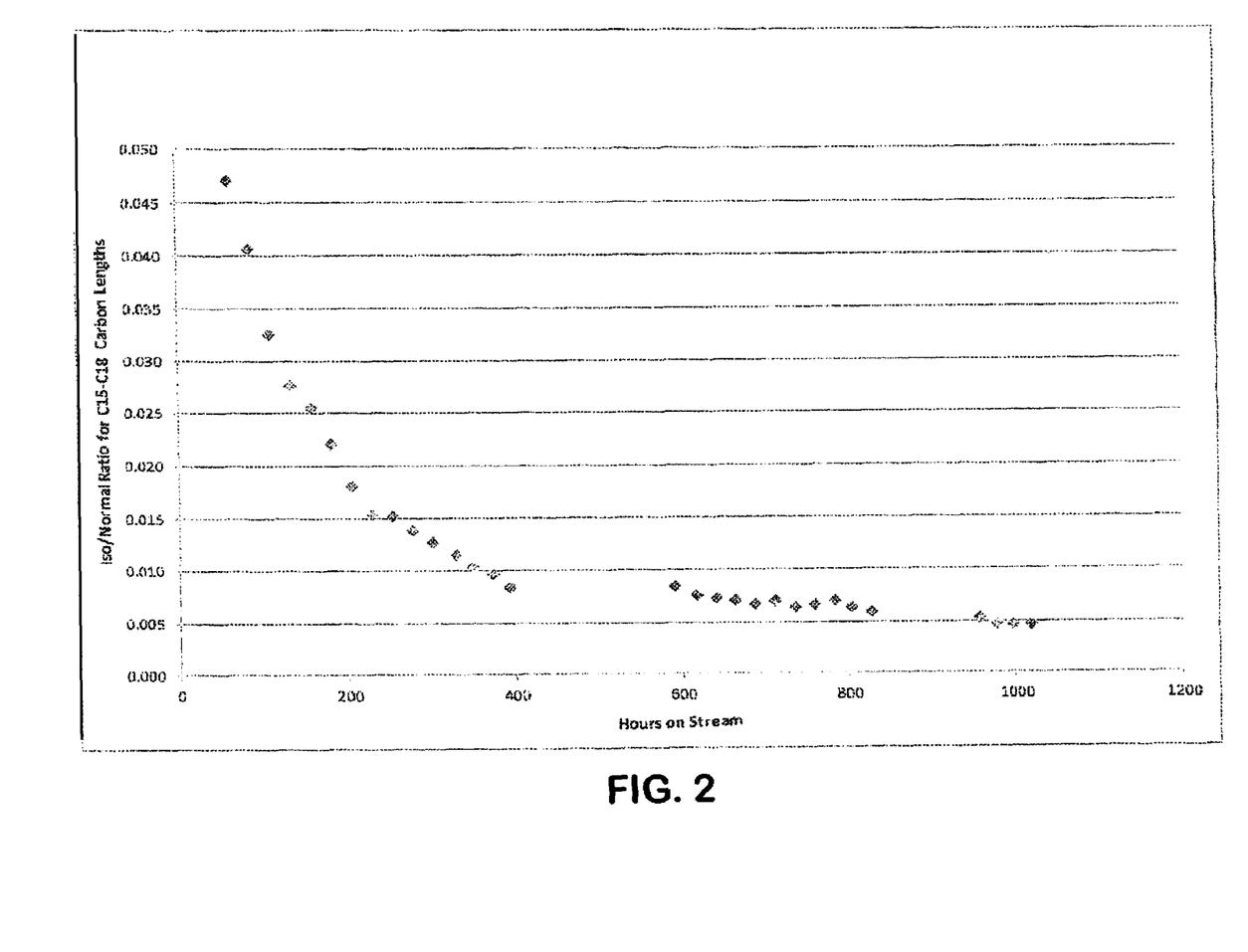
FIG. 2 is a plot of iso/normal ratio for C15-C18 carbon chain lengths versus hours on stream in accordance with Example 2.

A Ni—Mo catalyst was used to deoxygenate soybean oil. As shown in FIG. 2, while the isomerization activity was still high at the beginning of the run the linearity suffered. However, with time and this particular catalyst the isomerization activity decreased providing adequate linearity for the paraffin product to be used as a linear alkylbenzene precursor. The soybean oil is almost entirely composed of C16 and C18 fatty acid chains, so no subsequent cracking to shorten the resulting paraffins is required. Due to the clean nature of the feed, less than 2 wt. ppm nitrogen, the reactor could be run at a low temperature avoiding reaching isomerization activation temperature.

Example 3

Figure 3:
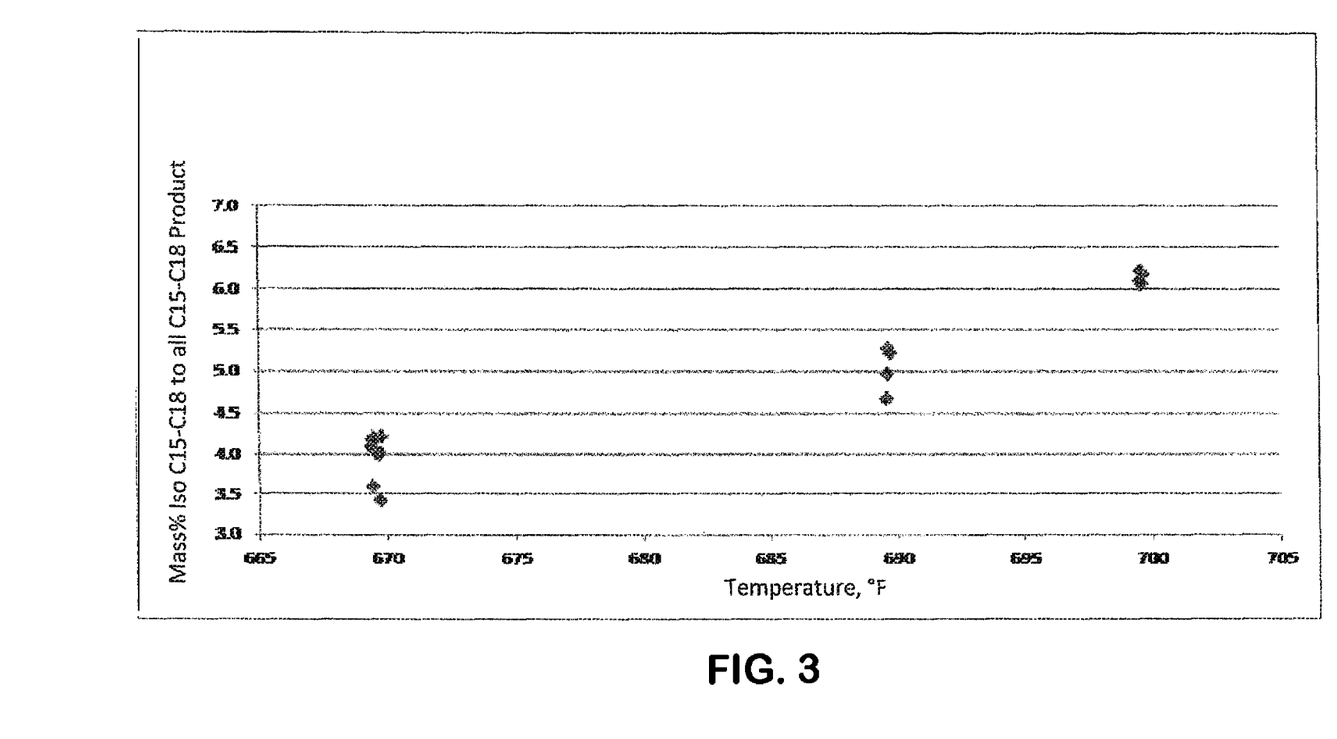
FIG. 3 is a plot of the mass percent iso C15-C18 carbon chain lengths of all C15-C18 product versus temperature in accordance with Example 3.

A more difficult to treat feedstock was run over two beds of Ni—Mo catalyst on alumina at a total LHSV of 0.33 hr$^{-1}$. The feed contained over 100 wt-ppm nitrogen. The feed was diluted 2:1 diluent:feed and run at elevated temperature to overcome the deoxygenation inhibition from the nitrogen. As shown in FIG. 3 the iso content of paraffins at the elevated operating temperatures resulted in at least 3.5 mass % non-linear paraffin, less than 96.5 mass % linearity, and increased with increasing temperature to 6 mass % as the catalyst deactivated and higher temperatures were required.

Example 4

Various deoxygenations at commercial scale, 250 bpd feed rate, were carried out on a variety of oils. The composite of these large scale runs shows a similar trend of nitrogen content of the feedstock versus isomerization of the generated paraffin and loss of linearity, see Table 2. The low nitrogen containing feeds, from palm and soy bean oil had iso/normal weight ratios of less than 0.1 while oils from higher nitrogen containing feedstocks from jatropha and camelina seed had iso/normal ratios greater than 0.1. For oils with naturally occurring high nitrogen content, refining the oil can reduce the nitrogen content to make it more suitable for highly linear paraffin production. Refining of the oil can reduce the nitrogen to make it more suitable for highly linear paraffin production.

TABLE 2

|  | Jatropha1 | Jatropha2 | Camelina1 | Camelina2 | Palm | Soy |
|---|---|---|---|---|---|---|
| C14-C22 Iso: Normal Ratio | 0.17 | 0.19 | 0.12 | 0.19 | 0.04 | 0.07 |
| Typical Feed Nitrogen Content (wt-ppm) | 18-31 | 18-31 | 9 | 9 | 3 | <1 |

Example 5

A coconut oil feed was deoxygenated, to form paraffins, dehydrogenated to form mono-olefins, and benzene was alkylated with the mono-olefins to form an alkylbenzene product with a modern carbon content of 62 mass % modern carbon as determined by ASTM D6866 as compared to a theoretical modern carbon content of 66.4 mass %, a bromine number of 1 g Br/per gram sample as determined by UOP standard test method 304, incorporated by reference, and a linearity of 92 mass %.

What is claimed is:

1. A method for generating an alkylbenzene product from a natural oil comprising:
deoxygenating feedstock comprising natural oil having less than about 3 wt. ppm of nitrogen contained in nitrogen containing compounds to form a stream comprising paraffins, wherein the deoxygenating utilizes a catalyst comprising a first component selected from the group consisting of Ni—Mo, Ni—Mo—P, Ni—Co—Mo, and Co—Mo and a second component selected from the group consisting of aluminas, titania, zirconia, and mixtures thereof;
dehydrogenating at least a portion of the paraffins to provide mono-olefins;
alkylating benzene with the mono-olefins under alkylation conditions to provide an alkylation effluent comprising alkylbenzenes and benzene;
separating the alkylbenzenes to provide the alkylbenzene product comprising alkylbenzenes having an alkyl group of about n carbon atoms where n is from 12 to about 13 and wherein the alkyl group is a linear alkyl group for at least 80 mass % of the alkylbenzenes having an alkyl group of about n carbon atoms.

2. The method of 1 further comprising, sulfonating the alkylbenzene product to form a linear alkylbenzene sulfonate product.

3. The method of claim 1 wherein a hydrogen stream results from dehydrogenating the paraffins, and wherein the method further comprises recycling the hydrogen stream to the deoxygenating step.

4. The method of claim 1 further comprising separating a second portion of paraffins from the stream comprising paraffins, and isomerizing the second portion of paraffins to form isoparaffins.

5. The method of claim 1 wherein di-olefins are also generated by dehydrogenating the paraffins, and wherein the method further comprises selectively hydrogenating the di-olefins to form additional mono-olefins.

6. The method of claim 1 wherein aromatics are also generated by dehydrogenating the paraffins, the method further comprising removing aromatics from the mono-olefins before alkylating.

7. A method for generating an alkylbenzene product from a natural oil comprising:
deoxygenating feedstock comprising natural oil having less than about 3 wt. ppm of nitrogen contained in nitrogen containing compounds to form a stream comprising paraffins, wherein the deoxygenating utilizes a catalyst comprising a first component selected from the group consisting of Ni—Mo, Ni—Mo—P, Ni—Co—Mo, and Co—Mo and a second component selected from the group consisting of aluminas, titania, zirconia, and mixtures thereof;
dehydrogenating at least a portion of the paraffins to provide mono-olefins;
alkylating benzene with the mono-olefins under alkylation conditions to provide an alkylation effluent comprising alkylbenzenes and benzene;
separating the alkylbenzenes to provide the alkylbenzene product comprising alkylbenzenes having an alkyl group of about n carbon atoms where n is from 8 to about 15 and wherein the alkyl group is a linear alkyl group for at least 80 mass % of the alkylbenzenes having an alkyl group of about n carbon atoms.

8. A method for generating an alkylbenzene product from a natural oil comprising:
deoxygenating feedstock comprising natural oil having less than about 3 wt. ppm of nitrogen contained in nitrogen containing compounds to form a stream comprising paraffins, wherein the deoxygenating utilizes a catalyst comprising a first component selected from the group consisting of Ni—Mo, Ni—Mo—P, Ni—Co—Mo, and Co—Mo and a second component selected from the group consisting of aluminas, titania, zirconia, and mixtures thereof;
dehydrogenating at least a portion of the paraffins to provide mono-olefins;
alkylating benzene with the mono-olefins under alkylation conditions to provide an alkylation effluent comprising alkylbenzenes and benzene;

separating the alkylbenzenes to provide the alkylbenzene product comprising alkylbenzenes having an alkyl group of about n carbon atoms where n is from 10 to about 13 and wherein the alkyl group is a linear alkyl group for at least 80 mass % of the alkylbenzenes having an alkyl group of about n carbon atoms.

9. A method for generating an alkylbenzene product from a natural oil comprising:

deoxygenating feedstock comprising natural oil having less than about 3 wt. ppm of nitrogen contained in nitrogen containing compounds to form a stream comprising paraffins, wherein the deoxygenating utilizes a catalyst comprising a first component selected from the group consisting of Ni—Mo, Ni—Mo—P, Ni—Co—Mo, and Co—Mo and a second component selected from the group consisting of aluminas, titania, zirconia, and mixtures thereof;

dehydrogenating at least a portion of the paraffins to provide mono-olefins;

alkylating benzene with the mono-olefins under alkylation conditions to provide an alkylation effluent comprising alkylbenzenes and benzene;

separating the alkylbenzenes to provide the alkylbenzene product comprising alkylbenzenes having an alkyl group of about n carbon atoms where n is from 9 to about 14 and wherein the alkyl group is a linear alkyl group for at least 80 mass % of the alkylbenzenes having an alkyl group of about n carbon atoms.

* * * * *